(12) United States Patent
Zhang et al.

(10) Patent No.: US 11,655,201 B2
(45) Date of Patent: May 23, 2023

(54) METHOD FOR PREPARING 2-TERT-BUTYL-4-METHOXYPHENOL AND NEW CRYSTAL FORM THEREOF

(71) Applicant: BIOMEDICAL ANALYSIS CENTER, ACADEMY OF MILITARY MEDICAL SCIENCES, Beijing (CN)

(72) Inventors: Xuemin Zhang, Beijing (CN); Xinhua He, Beijing (CN); Tao Zhou, Beijing (CN); Zhenggang Liu, Beijing (CN); Tao Li, Beijing (CN); Shengming Wu, Beijing (CN)

(73) Assignee: BIOMEDICAL ANALYSIS CENTER, ACADEMY OF MILITARY MEDICAL SCIENCES, Beijing (CN)

( * ) Notice: Subject to any disclaimer, the term of this patent is extended or adjusted under 35 U.S.C. 154(b) by 17 days.

(21) Appl. No.: 17/271,090

(22) PCT Filed: Mar. 23, 2018

(86) PCT No.: PCT/CN2018/080103
§ 371 (c)(1),
(2) Date: Feb. 24, 2021

(87) PCT Pub. No.: WO2018/214630
PCT Pub. Date: Nov. 29, 2018

(65) Prior Publication Data
US 2021/0317059 A1 Oct. 14, 2021

(30) Foreign Application Priority Data
May 24, 2017 (CN) .......................... 201710372606.1

(51) Int. Cl.
*C07C 43/23* (2006.01)
*C07C 41/40* (2006.01)
*C07C 41/09* (2006.01)

(52) U.S. Cl.
CPC .............. *C07C 43/23* (2013.01); *C07C 41/09* (2013.01); *C07C 41/40* (2013.01); *C07B 2200/13* (2013.01); *C07C 2601/16* (2017.05)

(58) Field of Classification Search
CPC ......... C07C 23/23; C07C 41/09; C07C 41/40; C07C 41/16; C07C 43/23; C07B 2200/13; A61K 31/05; A61K 31/085; A61P 35/00; A61P 37/02; A61P 37/06
See application file for complete search history.

(56) References Cited

U.S. PATENT DOCUMENTS

| | | | | |
|---|---|---|---|---|
| 5,041,425 A | * | 8/1991 | Hasegawa ............ | A61K 31/365 514/32 |
| 2005/0027018 A1 | * | 2/2005 | Remenar .................. | C07C 43/23 514/718 |
| 2008/0076825 A1 | * | 3/2008 | Bader ...................... | A61P 25/16 514/567 |
| 2009/0312582 A1 | * | 12/2009 | Rajadhyaksha ......... | C07C 41/16 568/650 |
| 2017/0260193 A1 | * | 9/2017 | Enlow .................... | A61K 9/5146 |

FOREIGN PATENT DOCUMENTS

| | | | | |
|---|---|---|---|---|
| CA | 2884784 A1 | * | 3/2014 | ........... A61K 31/192 |
| CN | 101583586 A | | 11/2009 | |
| CN | 101973858 A | | 2/2011 | |
| CN | 105017183 A | * | 11/2015 | ........... C07D 307/20 |
| CN | 105237517 A | * | 1/2016 | ........... C07D 403/14 |
| CN | 106279169 A | * | 1/2017 | ........... C07D 473/06 |
| CN | 106892864 A | * | 6/2017 | ........... C07D 213/75 |
| CN | 106986789 A | | 7/2017 | |
| WO | 2007/109654 A3 | | 9/2007 | |
| WO | WO-2011050638 A1 | * | 5/2011 | ........... C07C 405/00 |

OTHER PUBLICATIONS

Millipore Sigma (Petroleum ether, https://www.sigmaaldrich.com/US/en/product/vetec/v800295, 2022, 6 pages) (Year: 2022).*
Millipore Sigma (Petroleum ether, https://www.sigmaaldrich.com/US/en/product/vetec/v800295, Safety Data Sheet, Mar. 2007, 9 pages (Year: 2007).*
Millipore Sigma (Petroleum ether, first revision date Mar. 2007, https://www.sigmaaldrich.com/US/en/product/vetec/v800295, product info 6 pages and Safety Data Sheet, 9 pages) (Year: 2007).*
International Search Report issued in corresponding International Application No. PCT/CN2018/080103; dated Jun. 27, 2018; State Intellectual Property Office of the P.R. China, Beijing, China, 7 pgs.
Written Opinion issued in corresponding International Application No. PCT/CN2018/080103; dated Jun. 27, 2018; State Intellectual Property Office of the P.R. China, Beijing, China, 11 pgs.
Shindo, Ryodai, "Critical contribution of oxidative stress to TNFα-induced necroptosis downstream of RIPK1 activation"; Biochemical and Biophysical Research Communications; 436 (2013); pp. 212-216.
First Office Action issued in corresponding Chinese Application No. 201710372606 1; dated Dec. 24, 2019; 18 pgs.
(Continued)

*Primary Examiner* — Rosalynd A Keys
(74) *Attorney, Agent, or Firm* — Hauptman Ham, LLP

(57) ABSTRACT

The present invention relates to a stable crystal form, i.e. form A, of 2-tert-butyl-4-methoxyphenol, and to a new preparation method for the 2-tert-butyl-4-methoxyphenol; and the use of the 2-tert-butyl-4-methoxyphenol and the stable crystal form thereof, i.e. form A, in preparing antitumor drugs or immunomodulator drugs. The stable crystal form, i.e. form A, as expressed by a powder X-ray diffraction pattern in an angle of $2\theta$, using Cu-K$\alpha$ radiation, has at least 3 absorption peaks selected from the following positions: 6.27±0.10, 6.94±0.10, 12.27±0.10, 13.36±0.10, 14.01±0.10, 14.79±0.10, 15.31±0.10, 17.05±0.10, 18.30±0.10, 19.00±0.10, 20.47±0.10, 20.98±0.10, 22.37±0.10, 23.68±0.10, 24.55±0.10, 25.37±0.10, 30.83±0.10, 33.12±0.10, 40.50±0.10, 42.81±0.10.

8 Claims, 2 Drawing Sheets

(56) References Cited

OTHER PUBLICATIONS

Zhang, Yan, et al.; Progress in the Process Control of Pharmaceutical Polymorphism and Engineering; Chinese Journal of Pharmaceuticals 2018, 49(5); pp. 537-546 (see English Abstract).
Wang, Chang-he, et al.; Study on the preparation, characterization and solubility properties of different crystal forms of aripiprazole; China J. Pharma Anal 2020, 40(1); pp. 170-176 (see English Abstract).
Hansen, Thomas B., et al.; Polymorphic behavior of isonicotinamide in cooling crystallization from various solvents; Journal of Crystal Growth 450, 2016; pp. 81-90.

\* cited by examiner

METHOD FOR PREPARING 2-TERT-BUTYL-4-METHOXYPHENOL AND NEW CRYSTAL FORM THEREOF

RELATED APPLICATIONS

The present application is a National Phase of International Application Number PCT/CN2018/080103 filed Mar. 23, 2018 and claims priority to Chinese Application Number 201710372606.1 filed May 24, 2017.

FIELD OF THE INVENTION

The present invention relates to a stable crystal form, i.e. form A, of 2-tert-butyl-4-methoxyphenol, and to a new preparation method for the 2-tert-butyl-4-methoxyphenol; and use of the 2-tert-butyl-4-methoxyphenol and the stable crystal form thereof, i.e. form A, in preparing antitumor drugs or immunomodulator drugs.

BACKGROUND OF THE INVENTION

Recent studies have shown that antioxidants such as 2-tert-butyl-4-methoxyphenol (BHA), Apocynin, TEMPO, NAC and the like can inhibit the differentiation of monocytes into M2 macrophages by inhibiting the production of reactive oxygen species ROS, thereby inhibiting the occurrence of lung cancer in K-ras$^{LA2}$ model mice (Cell Research 2013, 23:898-914). However, there are also many studies showing that antioxidants can accelerate tumor growth, which is inconsistent with the anti-tumor activity of 2-tert-butyl-4-methoxyphenol in vivo. Therefore, inhibiting the production of ROS is one factor of 2-tert-butyl-4-methoxyphenol inhibiting the M2 polarization of TAMs, but not all. There are other mechanisms for BHA inhibiting M2 polarization of TAMs thus inhibiting tumor occurrence and development (Cancer Res. 1986, 46,165-168; Cancer Res., 1985, 45:1-8.). However, in contradiction to this, there is evidence showing that 2-tert-butyl-4-methoxyphenol has carcinogenic effects in early studies (Archives of Biochemistry and Biophysics 449 (2006) 171-177; Regulatory Toxicology and Pharmacology 47 (2007) 68-77; Food and Chemical Toxicology 38 (2000) 1075±1084). Therefore, there is a need for further research to evaluate the tumor treatment effect of 2-tert-butyl-4-methoxyphenol.

The inventors first verified the effect of 2-tert-butyl-4-methoxyphenol (BHA) in inhibiting the M2 polarization of macrophages, and confirmed the anti-tumor proliferation and metastasis effects of 2-tert-butyl-4-methoxyphenol in mouse models with lung cancer and breast cancer (CN 201610037849.5). At the same time, it was found through drug metabolism experiments that the in vivo half-life of BHA was very short, only 30-60 minutes. In addition, the inventors conducted toxicology experiments and found that for 600 mg/kg administration in mice, only part of the "hangover"-like central effect could be seen, which can be recovered after half an hour; for 1100 mg/kg administration in mice, half of the mice were lethal, and the toxic reaction symptoms disappeared after 30-60 minutes in the surviving mice. There was no toxic effect after long-term low-dose administrations in mice for 2 years. Therefore, combining with the research results of literature on the metabolites of 2-tert-butyl-4-methoxyphenol (with DNA damaging effects, Food and Chemical Toxicology 1999, 37: 1027-1038), it can be inferred that 2-tert-butyl-4-methoxyphenol itself has an anti-tumor effect, and the interaction of its metabolite tert-butylhydroquinone (TBHQ) with DNA may be the cause of its side effects. BHA has the potential to be developed into a drug.

However, the existing commercial BHA products are all mixtures of 2-tert-butyl-4-methoxyphenol (2-BHA) and 3-tert-butyl-4-methoxyphenol (3-BHA), with a content ratio of approximately 9:1-50:1. The inventors comparatively studied the antioxidant activities and macrophage polarization regulation activities of 2-tert-butyl-4-methoxyphenol and 3-tert-butyl-4-methoxyphenol. The results show that 2-tert-butyl 4-methoxyphenol has an antioxidant capacity of 2-3 times that of 3-tert-butyl-4-methoxyphenol, and has a macrophage polarization regulation activity of 5-100 times that of 3-tert-butyl-4-methoxyphenol. Therefore, the development of 2-tert-butyl-4-methoxyphenol as a medicine still needs to improve the purity.

The synthetic methods of 2-tert-butyl-4-methoxyphenol are mainly based on p-methoxyphenol, which is used as raw material, and tert-butanol, tert-butanol methyl ether or isobutylene to synthesize BHA under the catalysis of proton acid, ion exchange resin, aluminum alkoxide, aluminum oxide, etc. The product prepared by this method is a mixture of 2-BHA and 3-BHA. This method is also the main preparation method of commercial BHA (Sichuan Chemical Industry, 1989, 2, 55). A new method for synthesis of BHA was recently invented by a Korean patent. In this new method, 2-tert-butyl hydroquinone is used as a raw material, reacting with dimethyl sulfate to synthesize BHA under alkali catalysis in a water/n-hexane two-phase reaction system, to give a crude product with a yield of 96%, a purity of 89%. After recrystallization, the yield is 84%, and the purity is 99%, no isomer content reported (KR 2013051653).

SUMMARY OF THE INVENTION

One of the objectives of the present invention is to provide a method for preparing high-purity 2-tert-butyl-4-methoxyphenol (2-BHA).

The high-purity 2-tert-butyl-4-methoxyphenol (2-BHA) provided by the present invention has a purity of more than 99%, in which the content of the isomer 3-tert-butyl-4-methoxy phenol (3-BHA) is less than 1%.

The high-purity 2-tert-butyl-4-methoxyphenol (2-BHA) provided by the present invention has a purity of more than 99.0%, in which the content of the isomer 3-tert-butyl-4-methoxyphenol (3-BHA) is less than or equal to 0.5%.

The high-purity 2-tert-butyl-4-methoxyphenol (2-BHA) provided by the present invention has a purity of more than 99.0%, in which the content of the isomer 3-tert-butyl-4-methoxyphenol (3-BHA) is less than or equal to 0.2%.

A method for preparing the high-purity 2-tert-butyl-4-methoxyphenol (2-BHA) provided by the present invention is comprised of using the principle of steric hindrance under the action of a base with steric hindrance (steric base), selectively activating 4-position hydroxyl of 2-tert-butyl hydroquinone in an aprotic solvent, and then reacting with a methylating reagent to perform SN1 substitution reaction, and finally recrystallizing the reaction product to obtain the high purity 2-tert-Butyl-4-methoxyphenol (2-BHA). The reaction formula is shown in FIG. 1.

In the above method, after precise calculation of the spatial distance between the tert-butyl hydrogen atoms and the ortho hydroxyl group, the atomic radius or space volume of the commonly used bases for catalytic reactions, the steric base can be, but is not limited to, one or more selected from a group consisting of sodium hydride, potassium hydride, calcium hydride, potassium tert-butoxide, sodium hydroxide, potassium hydroxide and diisopropylethylamine. The base with unsatisfactory steric hindrance such as lithium hydride, lithium hydroxide, lithium carbonate, pyridine and the like is not used in the present invention.

In the above method, the aprotic solvent can be, but not limited to, one or more selected from a group consisting of tetrahydrofuran, dimethylformamide, dimethylacetamide, acetone, ethylene glycol dimethyl ether, dioxane, toluene, dichloromethane, and trichloromethane.

The solvent (aprotic solvent) selected in the present invention is conducive to not only the formation of salt between the 4-position hydroxyl group of 2-tert-butyl hydroquinone and the steric base, but also a SN1 substitution reaction of the formed salt with a methylating reagent. If water is produced when the base reacts with 2-tert-butyl hydroquinone, the generated water needs to be removed first.

The methylating reagent can be, but is not limited to, one or more selected from a group consisting of methyl iodide, dimethyl sulfate, dimethyl carbonate, and methyl bromide.

In the step of selectively activating of the above method, a ratio of the steric base to 2-tert-butyl hydroquinone may be 0.8-1.1:1.

The step of selectively activating may be performed under an ice-salt bath condition, and the time of selectively activating is 0.1-2.0 hours.

In the SN1 substitution reaction of the above method, a molar ratio of 2-tert-butyl hydroquinone to the reactive methyl group in the methylating reagent may be 1:0.7-1.1.

The SN1 substitution reaction may be performed under an ice-salt bath condition, and the time of the SN1 substitution reaction may be 0.5-24 hours.

The step of recrystallizing in the above method may use petroleum ether or a composite solvent containing more than 80% petroleum ether as the solvent for recrystallization.

The amount of solvent used for recrystallizing can be 1-10 times the volume of the crude 2-tert-butyl-4-methoxyphenol.

Another object of the present invention is to provide a stable crystal form of 2-tert-butyl-4-methoxyphenol (2-BHA) (hereinafter referred to as form A of 2-BHA).

The stable crystal form A of 2-tert-butyl-4-methoxyphenol (2-BHA) provided by the present invention, using Cu-Kα radiation, has a powder X-ray diffraction pattern expressed in 2θ angles having at least 3 absorption peaks selected from the following positions: 6.27±0.10, 6.94±0.10, 12.27±0.10, 13.36±0.10, 14.01±0.10, 14.79±0.10, 15.31±0.10, 17.05±0.10, 18.30±0.10, 19.00±0.10, 20.47±0.10, 20.98±0.10, 22.37±0.10, 23.68±0.10, 24.55±0.10, 25.37±0.10, 30.83±0.10, 33.12±0.10, 40.50±0.10, and 42.81±0.10.

The stable crystal form A of 2-tert-butyl-4-methoxyphenol (2-BHA) can be prepared by a method including the following steps: recrystallizing the crude 2-tert-butyl-4-methoxyphenol with petroleum ether or a composite solvent containing more than 80% petroleum ether.

In the method, the amount of the solvent used for recrystallizing can be 1-10 times the volume of crude 2-tert-butyl-4-methoxyphenol.

The mass content of 2-tert-butyl-4-methoxyphenol in the crude 2-tert-butyl-4-methoxyphenol is 98%-100%.

The stable crystal form A of 2-tert-butyl-4-methoxyphenol (2-BHA) provided by the present invention is easy to prepare, easy to purify, and has better physical and chemical stability than commercially available BHA. The stability is specifically manifested in its good fluidity, not easy to agglomerate, and not easy to oxidize and change color in the environment.

Another object of the present invention is to provide a pharmaceutical use of 2-tert-butyl-4-methoxyphenol and its stable crystal form A.

The use of 2-tert-butyl-4-methoxyphenol and its stable crystal form A provided by the present invention is the use of 2-tert-butyl-4-methoxyphenol and its stable crystal form A in the preparation of the following products:

1) anti-tumor drugs; 2) drugs for the treatment of autoimmune diseases; 3) immunomodulators.

In the above use, the autoimmune diseases include but are not limited to arthritis, rheumatism, lupus erythematosus, psoriasis, etc.

After intragastric administration in mice, form A of 2-tert-butyl-4-methoxyphenol (2-BHA) provided by the present invention has small individual differences in plasma concentration, and its maximum plasma concentration and lower area AUC of plasma concentration-time curve have a better correlation with the administration dose.

The present invention also provides a pharmaceutical composition, wherein each unit dose contains 1 mg-500 mg of high-purity 2-tert-butyl-4-methoxyphenol or 2-tert-butyl-4-methoxyphenol (2-BHA) of crystal form A as an active ingredient and a pharmaceutical excipient commonly used in the pharmaceutical field.

The present invention provides a pharmaceutical composition, wherein each unit dose contains 10 mg-250 mg of high-purity 2-tert-butyl-4-methoxyphenol or 2-tert-butyl-4-methoxyphenol (2-BHA) of crystal form A as an active ingredient and a pharmaceutical excipient commonly used in the pharmaceutical field.

The pharmaceutical composition according to the present invention may be in the following dosage forms: tablets such as but not limited to ordinary tablets, immediate-release tablets, sustained-release tablets, controlled-release tablets, film-coated tablets, sugar-coated tablets, buccal tablets, sublingual tablets, Bioadhesive tablets, etc.; capsules such as but not limited to hard capsules, soft capsules, etc.; injections such as but not limited to sterile or bacteriostatic-containing aqueous injections, oily injections, freeze-dried powder injections, injection microspheres, etc.; sprays agents such as but not limited to oral sprays, nasal sprays, topical skin sprays, etc.; aerosols such as but not limited to lung inhalation aerosols, topical skin aerosols, etc.; nasal drops such as but not limited to nasal drops solutions, gels for nasal drops, etc.; powder mists such as but not limited to powder mist for cavities, powder mist for nasal cavity, powder mist for topical skin, etc.; suppositories, patches, gels for other human cavities such as vagina, rectum, ear cavity, etc. The preparation process of these dosage forms can be prepared by those skilled in the art based on existing knowledge or reference to relevant textbooks or reference books or literature.

EMBODIMENT OF THE INVENTION

Figure 1:
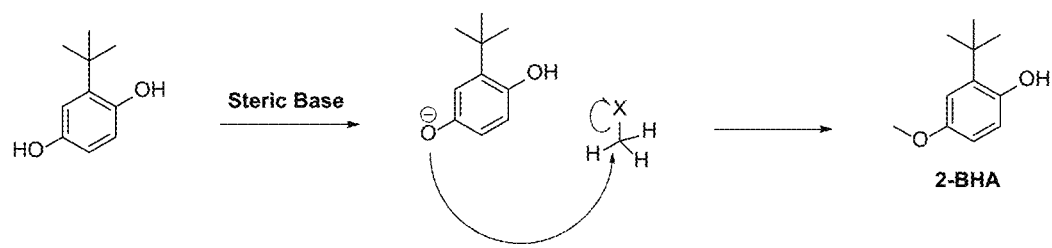
FIG. 1 shows a reaction formula for preparing high-purity 2-tert-butyl-4-methoxyphenol (2-BHA) of the present invention.

Unless otherwise specified, the experimental methods used in the following examples are conventional methods; unless otherwise specified, the reagents, biological materials, etc. used in the following examples can be obtained from commercial sources.

Example 1. New Preparation Method for 2-tert-butyl-4-methoxyphenol (2-BHA)

2-tert-butyl hydroquinone (0.78 g, 5 mmol) was dissolved in anhydrous tetrahydrofuran (5 mL), and then added into sodium hydride (0.12 g, 5 mmol) in tetrahydrofuran (10 mL) slowly in an ice salt bath under the protection of $N_2$ gas. After completing the addition, the resulting mixture was stirred for 30 minutes, followed by adding iodomethane (0.57 g, 4.5 mmol) dropwise, and then stirred overnight in an ice-salt bath. The reaction was quenched by adding saturated ammonium chloride solution. The reaction product was extracted with ethyl acetate (30 mL×3), washed with saturated brine three times, and recrystallized with petroleum ether (5 mL) to obtain a product with a yield of 78%. $^1$H NMR (400 MHz, $CDCl_3$) δ ppm 1.39 (s, 9H), 3.75 (s, 3H), 6.60 (d, J=1.12 Hz, 2H), 6.85-6.86 (m, 1H). MS (m/z)=181.1 (M+1).

Example 2. New Preparation Method for 2-tert-butyl-4-methoxyphenol (2-BHA)

2-tert-butyl hydroquinone (0.78 g, 5 mmol) was dissolved in anhydrous tetrahydrofuran (10 mL) in an ice-salt bath, and then added into potassium tert-butoxide (0.51 g, 4.5 mmol) in tetrahydrofuran (10 mL) slowly under the protection of $N_2$ gas. After completing the addition, the resulting mixture was stirred for 30 minutes, followed by adding dropwise iodomethane (0.57 g, 4.5 mmol), and then stirred overnight in an ice-salt bath. The reaction was quenched by adding saturated ammonium chloride solution. The reaction product was extracted with ethyl acetate (30 mL×3), washed with saturated brine three times, and recrystallized with petroleum ether (5 mL) to obtain a product with a yield of 85%.

Example 3. New Preparation Method Two for 2-tert-butyl-4-methoxyphenol (2-BHA)

2-tert-butyl hydroquinone (0.78 g, 5 mmol) was dissolved in anhydrous tetrahydrofuran (10 mL) in an ice-salt bath, and then added into diisopropylethylamine (0.70 g, 4.5 mmol) in tetrahydrofuran (10 mL) slowly under the protection of $N_2$ gas After completing the addition, the resulting mixture was stirred for 30 minutes, followed by adding dropwise iodomethane (0.57 g, 4.5 mmol), and then stirred overnight in an ice-salt bath. The reaction was quenched by adding saturated ammonium chloride solution. The reaction product was extracted with ethyl acetate (30 mL×3), washed with 1N hydrochloric acid (10 mL×3), washed with saturated aqueous sodium chloride solution 3 times, and recrystallized with petroleum ether to obtain a product with a yield of 80%.

Example 4. Preparation for Stable Crystal Form of 2-tert-butyl-4-methoxyphenol (2-BHA)

10 g of 2-tert-butyl-4-methoxyphenol (in which the mass content of 2-tert-butyl-4-methoxyphenol was 90% or the product prepared by any method in Examples 1-3) was added to petroleum ether (20 mL), heated and refluxed for 30 minutes, cooled naturally, filtered with suction, and dried in vacuum to obtain 9.5 g of white crystal with a yield of 95%.

Figure 2:
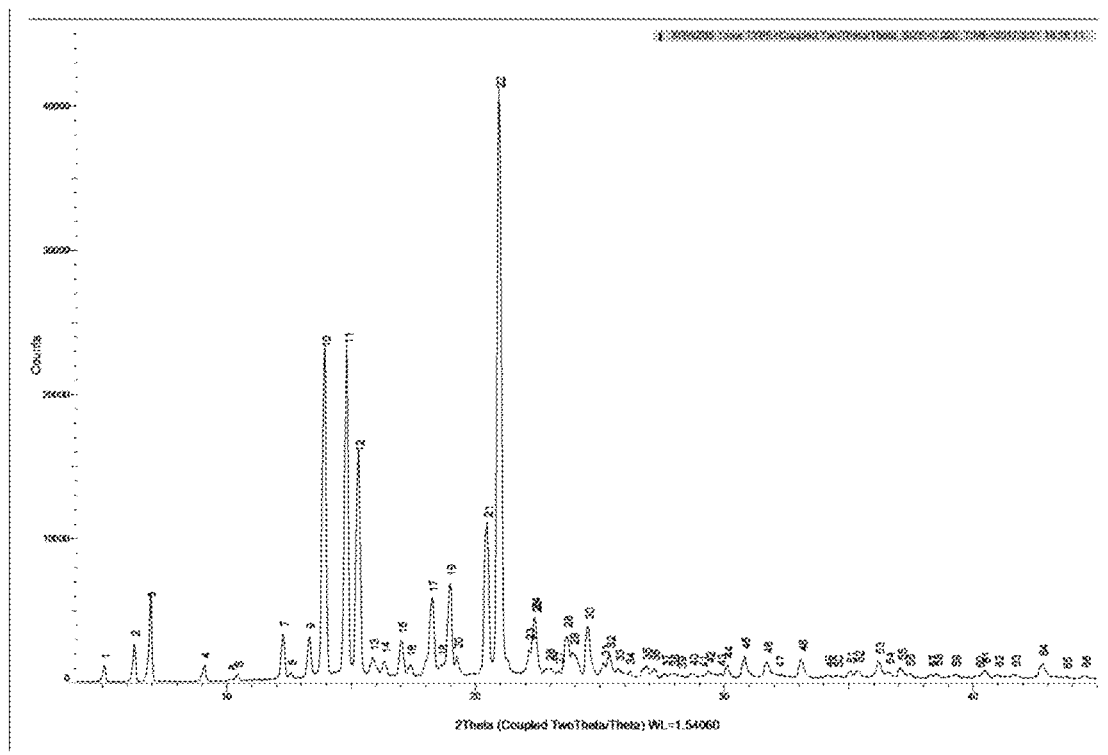
FIG. 2 is a graph showing an X-ray powder diffraction pattern of form A of 2-tert-butyl-4-methoxyphenol.

Crystal form determination: as expressed by a powder X-ray diffraction pattern in an angle of 2θ, using Cu-Kα radiation, there are 20 main absorption peaks (as shown in FIG. 2): 6.27±0.10, 6.94±0.10, 12.27±0.10, 13.36±0.10, 14.01±0.10, 14.79±0.10, 15.31±0.10, 17.05±0.10, 18.30±0.10, 19.00±0.10, 20.47±0.10, 20.98±0.10, 22.37±0.10, 23.68±0.10, 24.55±0.10, 25.37±0.10, 30.83±0.10, 33.12±0.10, 40.50±0.10, 42.81±0.10.

Example 5. Purity Analysis for 2-tert-butyl-4-methoxyphenol (2-BHA)

Figure 3:
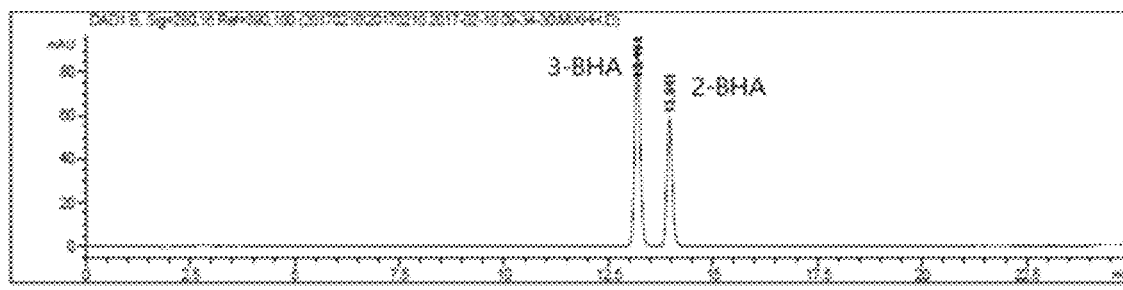
FIG. 3 is a graph showing a baseline separation analysis spectrum of 2-tert-butyl-4-methoxyphenol and its isomers.
Figure 4:
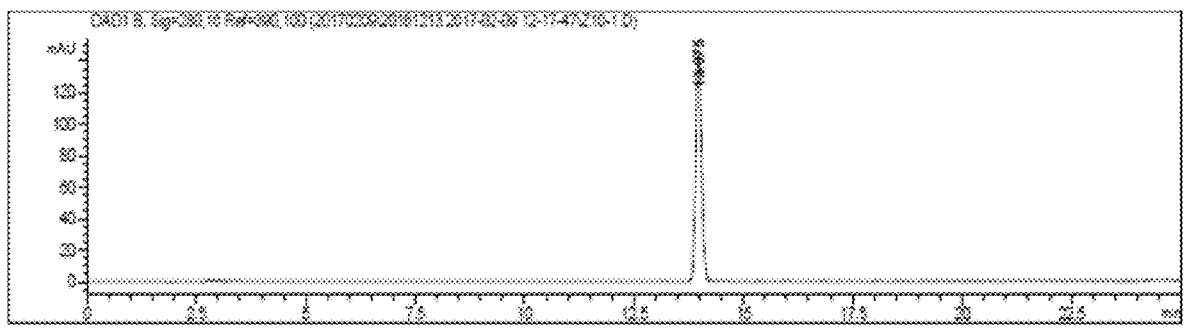
FIG. 4 is a graph showing an HPLC analysis spectrum of 2-tert-butyl-4-methoxyphenol prepared in Example 4.

The analysis method for 2-tert-butyl-4-methoxyphenol (2-BHA) and its isomer 3-tert-butyl-4-methoxyphenol (3-BHA) was established using High Performance Liquid Chromatography. Purities of the samples prepared by Example 1, Example 2, Example 3, and Example 4 were measured using stationary phase: C18, 250 mm, Φ5; mobile phase: methanol-water gradient (water phase 55%-10%, methanol 45%-90%). 2-tert-butyl-4-methoxyphenol (2-BHA) and its isomer 3-tert-butyl-4-methoxyphenol (3-BHA) were completely baseline separated (FIG. 3). The purity results of the freshly prepared 2-tert-butyl-4-methoxyphenol by the present invention are shown in Table 1 below, and the representative HPLC spectrum is shown in FIG. 4.

TABLE 1

Analysis results of 2-tert-butyl-4-methoxyphenol prepared by new method

|  | 2-BHA | 3-BHA |
| --- | --- | --- |
| Example 1 | >99.5% | not detected |
| Example 2 | >99.5% | <0.01% |
| Example 3 | >99.5% | <0.01% |
| Example 4 | 100% | not detected |

Example 6. Pharmacokinetic Evaluation of 2-tert-butyl-4-methoxyphenol (2-BHA) of Form A in Rats by Intragastric Administration SD rats, half male and half female, fasted overnight, 6 rats/group, were given 2-tert-butyl-4-methoxyphenol suspended in Tween 80 (2-BHA of form A prepared by Example 4) by intragastric administration, the dose being 100 mg/kg body weight. Before administration, and at 5 min, 30 min, 60 min, 120 min, 180 min, 300 min, 540 min, and 1200 min respectively after administration, blood was collected from fundus venous, and centrifuged, and then plasma was collected and stored at −20° C. The blood drug concentrations were measured at different time points, as shown in Table 2 below.

TABLE 2

Test results of plasma samples in the 100 mg/kg group given by intragastric administration (ng/mL)

| Blood sampling time | 1♂ | 2♂ | 3♂ | 4♀ | 5♀ | 6♀ |
|---|---|---|---|---|---|---|
| Predose | BLLOQ | BLLOQ | BLLOQ | BLLOQ | BLLOQ | BLLOQ |
| 5 min | 159.617 | 125.112 | 147.531 | 80.026 | 165.939 | 77.996 |
| 30 min | 694.651 | 489.006 | 359.028 | 157.878 | 371.466 | 240.870 |
| 1 h | 880.632 | 560.980 | 570.039 | 504.084 | 603.120 | 643.208 |
| 2 h | 267.167 | 267.234 | 312.997 | 687.296 | 410.399 | 199.206 |
| 4 h | 192.535 | 63.401 | 86.609 | 283.840 | 205.532 | 146.191 |
| 8 h | 117.919 | 27.328 | 192.532 | 78.447 | 42.984 | 121.700 |
| 24 h | BLLOQ | BLLOQ | BLLOQ | BLLOQ | BLLOQ | BLLOQ |

Note:
BLLOQ = below the detection limit

Example 7. Bulk Drug and Tablet Stability Test of 2-tert-butyl-4-methoxyphenol (2-BHA) of Form A An accelerated stability test for bulk drug was carried out directly from the crystal powder. An accelerated stability test for formulation was carried out on tablets.

Preparation process of formulation: form A of 2-tert-butyl-4-methoxyphenol (2-BHA) (form A of 2-BHA prepared in Example 4), microcrystalline cellulose, lactose and other auxiliary materials respectively were screened through 100 mesh, respectively for use. The prescription amount of form A of 2-tert-butyl-4-methoxyphenol, microcrystalline cellulose, lactose and other auxiliary materials were fully mixed according to the equal volume addition method. The above mixture was added to an aqueous solution of 2-3% polyvinylpyrrolidone under stirring, to obtain a soft material, which was screened through a 20-mesh sieve. The tablet weight regulator was adjusted to make the tablet weight being 250±10 mg, the hardness being 60-80 N, and then the tablet was compressed. After screening for dissolution, homogeneity and reproducibility and the like, the prescription was determined and 3 batches of samples were prepared.

The experimental results under stability accelerated test conditions (40° C.±2° C., RH 75%±5%) are shown in Table 3 and Table 4.

TABLE 3

Accelerated stability test for bulk drug

| Sample NO. | Acceleration time | Appearance | Content | Related substance |
|---|---|---|---|---|
| 20160808 | 0 month | white | 99.5% | 0.34% |
| | 1 month | white | 99.7% | 0.22% |
| | 2 month | white | 99.4% | 0.19% |
| | 3 month | white | 99.5% | 0.35% |
| 20160904 | 0 month | white | 99.8% | 0.14% |
| | 1 month | white | 99.7% | 0.21% |
| | 2 month | white | 99.3% | 0.39% |
| | 3 month | white | 99.3% | 0.35% |
| 20160908 | 0 month | white | 99.6% | 0.34% |
| | 1 month | white | 99.6% | 0.31% |
| | 2 month | white | 99.5% | 0.29% |
| | 3 month | white | 99.6% | 0.25% |
| Control: Commercially available 2-tert-butyl-4-methoxyphenol (TCI, J6ONAOT) | 0 month | off-white | 98.0% | 1.8% |
| | 1 month | light yellowish white | 95.1% | 3.9% |
| | 2 month | light yellowish + red particles | 92.1% | 8.8% |
| | 3 month | light yellowish red particles | 90.2% | 9.3% |

TABLE 4

Accelerated stability test for formulation

| Sample NO. | Acceleration time | Appearance | Content | Dissolution | Related substance |
|---|---|---|---|---|---|
| 20160918 | 0 month | white tablets, no obvious change in contents | 98.5% | 100.5% | 0.24% |
| | 1 month | white tablets, no obvious change in contents | 98.7% | 99.3% | 0.32% |
| | 2 month | white tablets, no obvious change in contents | 99.4% | 102.1% | 0.29% |
| | 3 month | white tablets, no obvious change in contents | 99.5% | 99.8% | 0.15% |
| 20161014 | 0 month | white tablets, no obvious change in contents | 99.8% | 99.2% | 0.14% |
| | 1 month | white tablets, no obvious change in contents | 99.7% | 98.9% | 0.21% |
| | 2 month | white tablets, no obvious change in contents | 99.3% | 100.2% | 0.29% |
| | 3 month | white tablets, no obvious change in contents | 99.3% | 99.9% | 0.33% |
| 20161108 | 0 month | white tablets, no obvious change in contents | 99.6% | 100.3% | 0.24% |
| | 1 month | white tablets, no obvious change in contents | 99.6% | 98.9% | 0.21% |
| | 2 month | white tablets, no obvious change in contents | 99.5% | 99.6% | 0.39% |
| | 3 month | white tablets, no obvious change in contents | 99.6% | 101.2% | 0.25% |

It can be seen that the crystal form has better stability during the preparation process.

INDUSTRIAL APPLICATION

The stable crystal form, i.e. form A, of 2-tert-butyl-4-methoxyphenol (2-BHA) provided by the present invention is easy to prepare, easy to purify, and has better physical and chemical stability than commercially available BHA. The stability is specifically manifested in its good fluidity, not easy to agglomerate, and not easy to oxidize and change color in the environment. After intragastric administration in mice, form A of 2-tert-butyl-4-methoxyphenol (2-BHA) provided by the present invention has small individual differences in plasma concentration, and its maximum plasma concentration and lower area AUC of plasma concentration-time curve have a better correlation with the administration dose.

The invention claimed is:

1. A stable crystalline form A of 2-tert-butyl-4-methoxyphenol, wherein: form A has a powder X-ray diffraction pattern expressed in 2θ angles using Cu-Kα radiation having absorption peaks selected from the following positions: 6.27±0.10, 6.94±0.10, 12.27±0.10, 13.36±0.10, 14.01±0.10, 14.79±0.10, 15.31±0.10, 17.05±0.10, 18.30±0.10, 19.00±0.10, 20.47±0.10, 20.98±0.10, 22.37±0.10, 23.68±0.10, 24.55±0.10, 25.37±0.10, 30.83±0.10, 33.12±0.10, 40.50±0.10, and 42.81±0.10.

2. The stable crystal form A of 2-tert-butyl-4-methoxyphenol according to claim 1, comprising
at least 98.0% 2-tert-butyl-4-methoxyphenol and less than 2.0% of 3-tert-butyl-4-methoxyphenol.

3. The stable crystal form A of 2-tert-butyl-4-methoxyphenol according to claim 1, comprising
at least 99.0% 2-tert-butyl-4-methoxyphenol and less than 1.0% of 3-tert-butyl-4-methoxyphenol.

4. The method for preparing the stable crystal form A of 2-tert-butyl-4-methoxyphenol according to claim 1, comprising the steps shown in (1) or (2):
(1) recrystallizing a crude 2-tert-butyl-4-methoxyphenol with petroleum ether or a composite solvent containing more than 80% petroleum ether to obtain the stable crystal form A of 2-tert-butyl-4-methoxyphenol;
(2) recrystallizing a crude 2-tert-butyl-4-methoxyphenol with petroleum ether or a composite solvent containing more than 80% petroleum ether as solvent to obtain a high-purity 2-tert-butyl-4-methoxyphenol, wherein the volume of solvent is 1-10 times the volume of the crude 2-tert-butyl-4-methoxyphenol, the chemical purity of 2-tert-butyl-4-methoxyphenol is more than 98%, and the content of the isomer 3-tert-butyl-4-methoxyphenol is less than or equal to 0.5%.

5. A pharmaceutical composition comprising the stable crystal form A of 2-tert-butyl-4-methoxyphenol according to claim 1 and a pharmaceutically acceptable adjuvant, diluent or carrier.

6. The pharmaceutical composition according to claim 5, wherein:
the pharmaceutical composition is used as anti-tumor drugs, drugs for the treatment of autoimmune diseases or immunomodulators.

7. The pharmaceutical composition according to claim 5, wherein:
the dosage of the stable crystal form of 2-tert-butyl-4-methoxyphenol is 50-1000 mg per person per day.

8. The pharmaceutical composition according to claim 5, wherein:
the dosage of the stable crystal form of 2-tert-butyl-4-methoxyphenol is 100-800 mg per person per day.

* * * * *